United States Patent [19]

Lehtikoski et al.

[11] Patent Number: 4,771,631
[45] Date of Patent: Sep. 20, 1988

[54] DEVICE FOR MEASURING THE MOISTURE CONTENT AND BASIC WEIGHT OF PAPER

[76] Inventors: Olavi Lehtikoski, Sölvenkatu 8, 78300, Varkaus; Martti Nissinen, Kirvesniementie 2, SF-78880, Kuvansi, both of Finland

[21] Appl. No.: 798,700

[22] Filed: Nov. 15, 1985

[30] Foreign Application Priority Data

Nov. 16, 1984 [FI] Finland .................................. 844500

[51] Int. Cl.⁴ .................. G01N 5/04; G01N 25/56; G01N 1/02
[52] U.S. Cl. ........................................... 73/73; 73/76; 162/198; 162/263; 177/50; 83/77
[58] Field of Search .................. 73/76, 73, 864.41; 83/685, 690, 694, 522, 73, 77, 697; 177/50, 245; 364/554, 567, 568; 162/49, 198, 263

[56] References Cited

U.S. PATENT DOCUMENTS

| | | | |
|---|---|---|---|
| 2,789,640 | 4/1957 | Belden | 83/690 |
| 2,853,133 | 9/1958 | Norman | 73/864.41 |
| 2,873,605 | 1/1959 | Warner | 73/73 |
| 3,181,405 | 5/1965 | Coy | 83/690 |
| 3,532,016 | 10/1970 | Lane | 83/685 |
| 3,536,258 | 10/1970 | Rocheleau | 364/568 |
| 3,857,023 | 12/1974 | McCall | 364/568 |
| 3,993,148 | 11/1976 | Keser et al. | 83/73 |
| 4,165,633 | 8/1979 | Raisanen | 73/76 |
| 4,312,219 | 1/1982 | Lee et al. | 73/76 |
| 4,316,384 | 2/1982 | Pommer et al. | 73/76 |
| 4,341,735 | 7/1972 | Seifried | 422/66 |
| 4,374,703 | 2/1983 | Lebeau et al. | 364/568 |
| 4,485,284 | 11/1984 | Pakulis | 73/76 |

FOREIGN PATENT DOCUMENTS 1191141  4/1965  Fed. Rep. of Germany .......... 73/76

Primary Examiner—William A. Cuchlinski, Jr.
Assistant Examiner—Patrick R. Scanlon
Attorney, Agent, or Firm—Andrus, Sceales, Starke & Sawall

[57] ABSTRACT

A device for measuring the moisture content and basic weight of paper in a gravimetric and more accurate manner than before. The device includes a cutting device for cutting the sample from a specimen sheet, a balance for weighing the sample, a computer for computing the moisture content and the basic weight of the sample, an output device for printing out the results of the moisture content and basic weight as well as a controller for controlling the device automatically and advantageously a drying device for drying the sample.

6 Claims, 1 Drawing Sheet

DEVICE FOR MEASURING THE MOISTURE CONTENT AND BASIC WEIGHT OF PAPER

BACKGROUND OF THE INVENTION

The object of the invention is a device for measuring the moisture content and/or the basic weight of paper. The device in accordance with the invention is meant especially for the gravimetric and automatic determination of the quantities in question.

The moisture content and/or basic weight of paper is usually determined in a laboratory by weighing the paper sample, when it is moist and dry as well as by calculating the required quantities by using the weighing results and measurements of the sample as a basis. In addition, on-line methods are known for determining the moisture content and/or the basic weight of the paper directly from the paper web for example by the aid of optical quantities, such as I.R. radiation, and radioactive quantities. The calibration of the measuring devices for example by gravimetric methods is a prerequisite for the use of these on-line methods. In addition, the current on-line methods don't give sufficiently accurate results, when striving for moisture content and basic weight measurements which would have the same order of accuracy as the laboratory methods.

SUMMARY OF THE INVENTION

The object of the present invention is to provide a device for the automatic determination of the moisture content and basic weight of paper, which device is more accurate than the current on-line devices and quicker than the laboratory methods.

The invention is based upon an automatically operative measuring device, including control elements for automatic control. The device includes members for cutting a sample of a certain size from the sample sheet as well as for weighing the sample and printing the results out. In addition, a drying device is advantageously included within the measuring device for drying the sample and thus determining the moisture content and basic weight of the sample accurately.

The cutting blade has been conveniently shaped into a tubelike form and a drying device, such as an I.R. radiator, has been placed within the blade so that the blade forms a cover for the sample and, thus creates consistent measuring circumstances for the weighing.

The balance has been arranged advantageously to weigh the sample continuously as the drying device dries the sample at the same time, and a computing unit has been arranged conveniently to calculate the weight of the dried material after a certain drying period by using the information of the quality of the sample and by weight extrapolation during the period, at which the weight of the sample changes due to the drying.

The device in accordance with the invention is highly accurate due to its gravimetric principle of functioning; and an accuracy of even 0.1% can be achieved by the device. The actuation of the device, i.e. the functioning in order to measure the moisture content and/or the basic weight of the paper sample takes place automatically and in an exceedingly quick manner, for example during 1 min. or even faster. Thus, the device is better suited for the calibration of the on-line measuring instruments than the laboratory methods used nowedays.

DESCRIPTION OF THE DRAWINGS

The invention is explained in detail hereinafter by the aid of examples and by referring to the accompanying drawings, in which.

DESCRIPTION OF THE ILLUSTRATED EMBODIMENT

Figure 1:
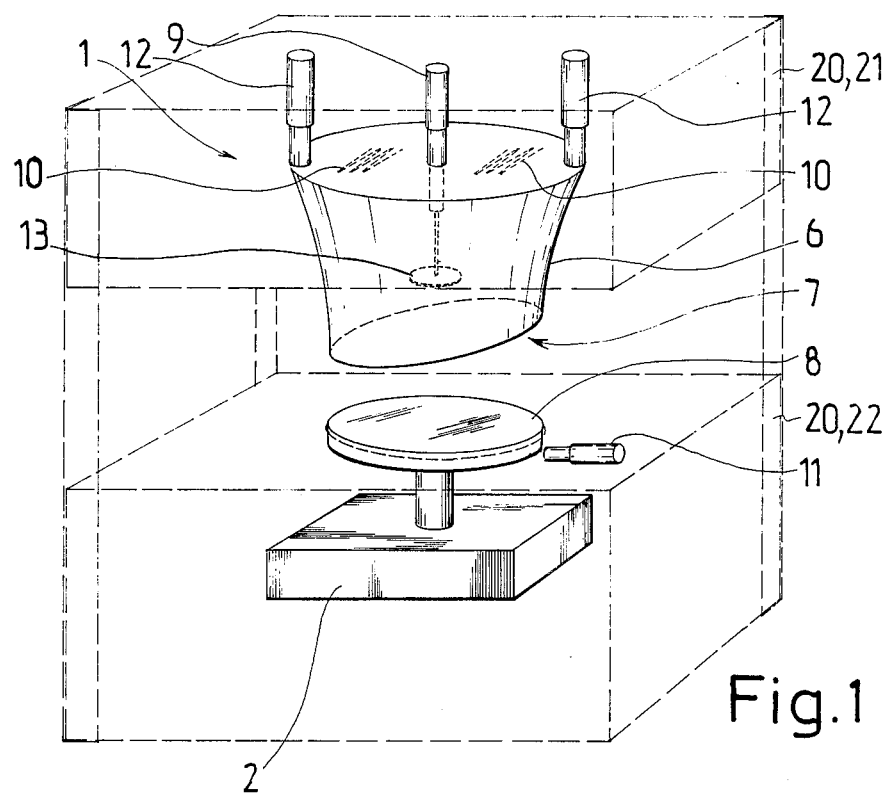
FIG. 1 shows a diagramatic view of the device in accordance with the invention viewed in an angle from above and prsented in a simplified manner for clarifying the structure of the device.

FIG. 1 shows a device in accordance with the invention for determining the moisture content and/or the basic weight i.e. dry weight of the paper. The device includes a frame 20, a cutting device/unit 1 for cutting a sample from the specimen sheet and a balance 2 for weighing the sample, a computer 3, an output device 4 and a controller 5 which have not been shown in this figure in order to clarify the structure (the control unit has been shown in the block diagram FIG. 2).

The cutting unit of the device, shown in FIG. 1, includes a tube- or spoutlike cutting blade 6 which lower cross-sectional edge forms a circular cutting edge 7. The cutting blade becomes wider, when moving away from the cutting edge i.e. when moving upwards from the cutting edge as shown in the adaptation of FIG. 1. The cutting blade 6 has been placed inside the upper module 21 of the frame, and the edge 7 has been directed downwards. The cutting edge is movable from the top downwards and vice versa by the aid of a power unit such as hydraulic cylinders 12.

The cutting device 1 includes a cutting base 8 which is formed of the weighing base of the balance 2. The cutting base is mainly of the same form as the cutting edge and adapted to fit through the cutting edge as the cutting edge is arranged to cut a sample from the specimen sheet against the cutting base, when the cutting edge is pressed downwards and past the cutting base.

In addition, a compressing member 9, i.e. a hydraulic or pneumatic cylinder with its compressing ends 13 has been included within the cutting unit. The compressing ends have been arranged to press the specimen sheet against the cutting base as the cutting of the sample takes place. In the presented adaptation the cutting base has been equipped with a clamping member or clamping bar 11 for clamping the base into its place for the time taken to cut the sample.

In additon, FIG. 1 shows two drying devices 10 placed within the cutting blade, i.e. I.R. radiators or coiled resistance wires which dry the sample inside the tubelike cutting blade in a positon shielded and separated from the surroundings, after the sample has been cut of.

Figure 2:
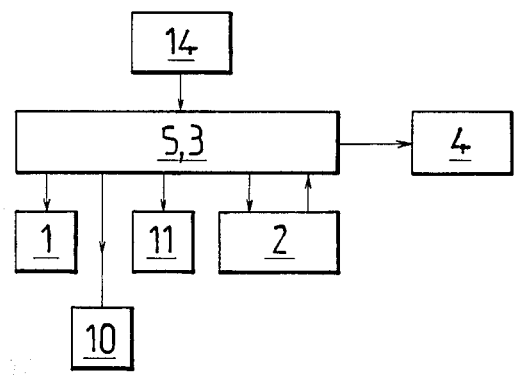
FIG. 2 shows a block dagram of the device in accordance with FIG. 1.

FIG. 2 shows a block diagram of the device. The device includes a controller 5 with its computer 3 such as a microprocessor. The controller has been arranged to control the following operations, the operation of the cutting unit in order to cut the sample, the operation of the drying device 10 in order to dry the sample, the operation of the actuating i.e. locking device 11 in order to lock the cutting base 8 i.e. the weighing base of the balance into its place for the time taken to cut the sample as well as the operation of the balance 2 in order to determine the weight of the sample cut and situated on the cutting base 8.

In addition, the controller-computer 5, 3 gives the output of the final results by an output device 4, for example by a printer in the form of written information, as an electrical signal for the control of the process or as a display on a displaying device.

Figure 3:
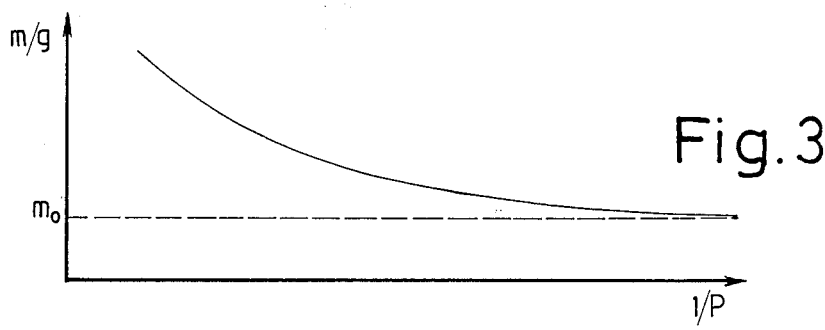
FIG. 3 shows the determination of the basic weight of a paper sample by using a device in accordance with the present invention.

When actuating the device shown in FIGS. 1-2, the paper sample is guided onto the cutting base between the jaws. The jaws have been formed between the upper and lower modules, and the guidance is effected manually or by for example the usual types of sheet displacement devices such as rolls, jaws or other like devices. Afterwards the device is started by the starter 14 of the controller 5 either manually or by a starting switch or automaticlly by a sample detector such as a photocell. Thus, the controller actuates the cutting device 1 i.e. the cylinders 12 operable by a pressurized medium, liquid or gas, move the cutting blade downwards as at the same time the actuating member 11 locks the base 8 into its place and as the compressing member 9 presses the paper against the base 8. At this moment the cutting edge 7 of the cutting blade cuts a sample of a certain size from the specimen sheet, and the sample remains above the base 8 within the cover of the tube-like blade 6. Then the compressing member 9 moves upwards and the actuating member 11 releases the weighing base of the balance which weighs and indicates the initial weight of the sample. Afterwards, the controller switches on the electric current through the heating coils of the drying device 10. The sample starts to dry up due to the action of the heating coils as the balance continuously monitors the weight of the sample. The weight of the sample decreases exponentially according to FIG. 3 and the weight approaches the dry weight $m_o$ of the sample. The computer 3 monitors the development of the weight and computes the weight of the sample according to a programe included in it. This takes place after monitoring the weight of the sample for a certain period of time for example from approximately 10 s. to 10 min. Lastly the output device 4 prints out the value of the basic i.e. dry weight of the sample.

The computer 3 can be, if desired, programmed to determine the moisture content of the sample in for example percentages. At this moment the operation takes place mechanically similarly to the determination of the basic weight of the sample. Lastly, the computer has been programmed to give the moisture content of the sample as the result i.e. (initial weight—basic weight)×100.

The example presented in FIGS. 1-2 is only intended for the clarification of the invention, and one or some of the parts presented in the example can be replaced by any corresponding parts for effecting the corresponding operations. Thus, the cutting blade could be stationary and the weighing base could have been arranged to rise upwards to press the sample sheet against the cutting edge 7, which could naturally render the actuating-clamping device needless. Further, instead of the cover formed by the cutting blade the device could include any cover including blowers and/or ventilating openings, for ensuring constant drying circumstances for the weighing of the sample and for enhancing the drying. Moreover, mechanisms such as the hydraulicly or pneumatically pessurized systems for operating the parts of the power unit have not been explained in detail; in this case reference is made to generally known corresponding mechanisms. In addition, the controller-computer has not been described in detail in order to clarify the structure of the device. Any known control- or computing devices can be used.

What we claim is:

1. A device for measuring the basic weight of a sample of a fibrous material impregnated with a liquid, comprising weighing means for determining the weight of a sample and having a sample supporting base, releasable locking means operably connected to said weighing means and having a locked position wherein said weighing means is inoperable and having an unlocked position wherein said weighing means will weigh a sample disposed on said base, sample cutting means disposed above the base for cutting a sample from a sheet, a cover connected to the cutting means for enclosing the cut sample, drying means disposed within the cover, and operating means connected to the cover for moving the cover and the cutting means in a direction towards said base to cut a sample from said sheet and to move said cover and said cutting means in the opposite direction to release said sample.

2. The device of claim 1, wherein said drying means comprises an infrared heater.

3. The device of claim 1, and including pressure means disposed within said cover for pressing said sheet against said base during cutting of said sample from said sheet.

4. The device of claim 1, and including computer means to calculate the basic weight and moisture content of said sample after a predetermined drying period by using the weight change during the drying period.

5. The device of claim 1, wherein said cutting means includes a generally circular blade.

6. The device of claim 5, wherein said cover extends upwardly from said blade and includes an upwardly diverging side wall and a top wall.

* * * * *